United States Patent
Lee et al.

(10) Patent No.: US 9,211,079 B2
(45) Date of Patent: Dec. 15, 2015

(54) BIOELECTRICAL IMPEDANCE MEASUREMENT APPARATUS

(71) Applicant: Tatung Company, Taipei (TW)

(72) Inventors: Chao-Fa Lee, Taipei (TW); Shih-Jung Chang, Taipei (TW); Yu-Shen Lee, Taipei (TW)

(73) Assignee: Tatung Company, Taipei (TW)

( * ) Notice: Subject to any disclaimer, the term of this patent is extended or adjusted under 35 U.S.C. 154(b) by 292 days.

(21) Appl. No.: 13/917,617

(22) Filed: Jun. 13, 2013

(65) Prior Publication Data

US 2014/0288457 A1 Sep. 25, 2014

(30) Foreign Application Priority Data

Mar. 19, 2013 (TW) .............................. 102109661 A

(51) Int. Cl.
*A61B 5/00* (2006.01)
*A61B 5/053* (2006.01)

(52) U.S. Cl.
CPC .............. *A61B 5/053* (2013.01); *A61B 5/0531* (2013.01); *A61B 5/4872* (2013.01); *A61B 5/6897* (2013.01); *A61B 5/6898* (2013.01); *A61B 5/7228* (2013.01); *A61B 5/742* (2013.01)

(58) Field of Classification Search
CPC .......... A61B 5/03; A61B 5/0537; A61B 5/04; A61B 5/053; A61B 5/0532
See application file for complete search history.

(56) References Cited

U.S. PATENT DOCUMENTS

| 7,557,311 | B2 * | 7/2009 | Umemoto | 177/25.16 |
| 9,030,211 | B2 * | 5/2015 | Cloutier et al. | 324/601 |
| 9,042,975 | B2 * | 5/2015 | Gregory | 600/547 |
| 9,042,976 | B2 * | 5/2015 | Slizynski et al. | 600/547 |

FOREIGN PATENT DOCUMENTS

| CN | 2790408 | 6/2006 |
| TW | 200412897 | 8/2004 |
| TW | 200501923 | 1/2005 |
| TW | 200614769 | 5/2006 |
| TW | I255705 | 6/2006 |
| TW | I260147 | 8/2006 |
| TW | I278305 | 4/2007 |
| TW | I292276 | 1/2008 |
| TW | I316401 | 11/2009 |
| TW | M422126 | 2/2012 |
| TW | 201215372 | 4/2012 |

OTHER PUBLICATIONS

"Office Action of Taiwan Counterpart Application", issued on Feb. 3, 2015, p. 1-p. 5.

* cited by examiner

*Primary Examiner* — Max Hindenburg
(74) *Attorney, Agent, or Firm* — Jianq Chyun IP Office

(57) ABSTRACT

A bioelectrical impedance measurement apparatus is provided. A power signal and a frequency regulation signal for driving a measurement unit of the bioelectrical impedance measurement apparatus to perform bioelectrical impedance measurement are provided through a first sound channel output terminal and a second sound channel output terminal of a host device, and a bioelectrical impedance measurement result is received by a microphone input terminal of the host device.

8 Claims, 3 Drawing Sheets

BIOELECTRICAL IMPEDANCE MEASUREMENT APPARATUS

CROSS-REFERENCE TO RELATED APPLICATION

This application claims the priority benefit of Taiwan application serial no. 102109661, filed on Mar. 19, 2013. The entirety of the above-mentioned patent application is hereby incorporated by reference herein and made a part of this specification.

BACKGROUND

1. Technical Field

The invention relates to a measurement apparatus. Particularly, the invention relates to a bioelectrical impedance measurement apparatus.

2. Related Art

Since measurement analysis of bioelectrical impedance has advantages of simple, rapid, accurate, non-invasive, no radiation damage, low cost and real-time and continuous monitoring, etc., it has been widely used in different tests, for example, enzymatic reaction of biotech, blood test, human acupoint test and body fat test, etc., which all belong to application of the bioelectrical impedance analysis, and operation frequencies in test analysis of different test projects are different.

A plurality of bioelectrical impedance measurement apparatuses have been developed, though each of the apparatuses is only adapted to a specific purpose, and a bioelectrical impedance measurement apparatus capable of switching between different test modes based on bioelectrical impedance measurement principle and being used in collaboration with a portable electronic apparatus such as a mobile phone, a tablet PC or a notebook computer is still not developed.

SUMMARY

The invention is directed to a bioelectrical impedance measurement apparatus, which is capable of implementing a plurality of bioelectrical impedance measurements, and is capable of being used in collaboration with a portable electronic apparatus such as a mobile phone, a tablet PC or a notebook computer, and has characteristics of lightness, slimness, shortness and smallness and is easy to use.

The invention provides a bioelectrical impedance measurement apparatus including a measuring device and a host device. The host device is coupled to the measuring device, and has a first sound channel output terminal, a second sound channel output terminal and a microphone input terminal. An alternating current (AC) power signal and a frequency regulation signal are respectively output to the measuring device through the first sound channel output terminal and the second sound channel output terminal according to a measurement mode of the host device, so as to drive the measuring device to perform bioelectrical impedance measurement on an object to be tested, and a measurement result of the object to be tested is received through the microphone input terminal, so as to analyse the same to obtain biomedical information.

In an embodiment of the invention, the measuring device includes a regulation unit, a driving unit, a measurement unit and a mixing unit. The regulation unit is coupled to the first sound channel output terminal and the driving unit, and regulates the AC power signal to provide a direct current (DC) power signal to the driving unit. The driving unit is coupled to the host device, and outputs a driving signal according to the frequency regulation signal and the DC power signal. The measurement unit is coupled to the driving unit, and is driven by the driving signal to measure the object to be tested, and outputs a measurement signal. The mixing unit is coupled to the microphone input terminal, the first sound channel output terminal and the measurement unit, and mixes the AC power signal and the measurement signal to produce a mixed signal and output the same to the microphone input terminal. The host device analyses the mixed signal to obtain the biomedical information.

In an embodiment of the invention, the driving unit includes a transistor, a resistor and a bipolar transistor. A drain and a source of the transistor are respectively coupled to the regulation unit and the measurement unit. The resistor is coupled between a gate of the transistor and a ground. An emitter of the bipolar transistor is coupled to the regulation unit, a collector of the bipolar transistor is coupled to the gate of the transistor, and a base of the bipolar transistor is coupled to the second sound channel output terminal.

In an embodiment of the invention, the regulation unit includes a first diode, a first capacitor, a second diode and a second capacitor. An anode of the first diode is coupled to the first sound channel output terminal, a cathode of the first diode is coupled to the driving unit, and the first diode provides the DC power signal to the driving unit through the cathode. The first capacitor is coupled between the cathode of the first diode and the ground. A cathode of the second diode is coupled to the anode of the first diode. The second capacitor is coupled between an anode of the second diode and the ground.

In an embodiment of the invention, the mixing unit includes an operation amplifier, a capacitor, a resistor and a transistor. A positive input terminal of the operation amplifier is coupled to the first sound channel output terminal. The capacitor is coupled between an output terminal of the operation amplifier and the microphone input terminal. The resistor is coupled between a negative input terminal and the output terminal of the operation amplifier. The transistor is coupled between the negative input terminal of the operation amplifier and the ground, and a gate of the transistor is coupled to an output terminal of the measurement unit.

In an embodiment of the invention, the host device further includes a display unit to display the biomedical information.

In an embodiment of the invention, the host device includes a mobile phone, a tablet PC or a notebook computer.

In an embodiment of the invention, the measurement mode includes an acupoint detection mode, a body fat measuring mode or a bio-detection mode.

According to the above descriptions, the power signal and the frequency regulation signal required for driving the measurement unit to perform measurement are provided through the first sound channel output terminal and the second sound channel output terminal of the host device, and the microphone input terminal of the host device is used to receive the measurement result, such that the host device can analyse the measurement result to obtain the biomedical information. In this way, the bioelectrical impedance measurement apparatus is adapted to multiple test projects, and can be used in collaboration with a portable electronic apparatus such as a mobile phone, a tablet PC or a notebook computer, and has characteristics of lightness, slimness, shortness and smallness and is easy to use.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
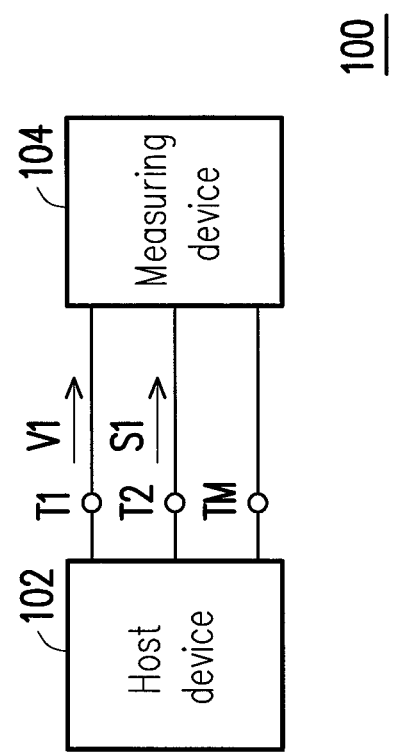
FIG. 1 is a schematic diagram of a bioelectrical impedance measurement apparatus according to an embodiment of the invention.

FIG. 1 is a schematic diagram of a bioelectrical impedance measurement apparatus according to an embodiment of the invention. Referring to FIG. 1, the bioelectrical impedance measurement apparatus 100 includes a host device 102 and a measuring device 104, where the host device 102 is, for example, portable electronic device such as a mobile phone, a tablet PC, or a notebook computer, etc., which has a sound channel output terminal T1, a sound channel output terminal T2 and a microphone input terminal TM. The host device 102 is coupled to the measuring device 104, which respectively outputs an alternating current (AC) power signal V1 and a frequency regulation signal S1 to the measuring device 104 through the sound channel output terminal T1 and the sound channel output terminal T2 according to a measurement mode of the host device 102, so as to drive the measuring device 104 to perform bioelectrical impedance measurement (for example, human acupoint detection, body fat measurement, skin humidity detection, etc.) on an object to be tested (for example, different parts of the body), where the measurement mode may include an acupoint detection mode, a body fat measuring mode and a bio-detection mode, etc. Moreover, the host device 102 further receives a measurement result of the object to be tested from the measuring device 104 through the microphone input terminal TM, and analyses the measurement result to obtain biomedical information, for example, an acupoint skin impedance value and a body fat rate, etc.

In this way, the power signal and the frequency modulation signal are provided through the sound channel output terminal T1 and the sound channel output terminal T2 of the host device 102, and the measurement result is received by the microphone input terminal TM of the host device 102, such that the host device 102 can analyse the measurement result to obtain the biomedical information. In this way, the bioelectrical impedance measurement apparatus 100 is adapted to a plurality of test projects of different frequencies, and can be used in collaboration with a portable electronic apparatus such as a mobile phone, a tablet PC or a notebook computer, and has characteristics of lightness, slimness, shortness and smallness and is easy to use.

Figure 2:
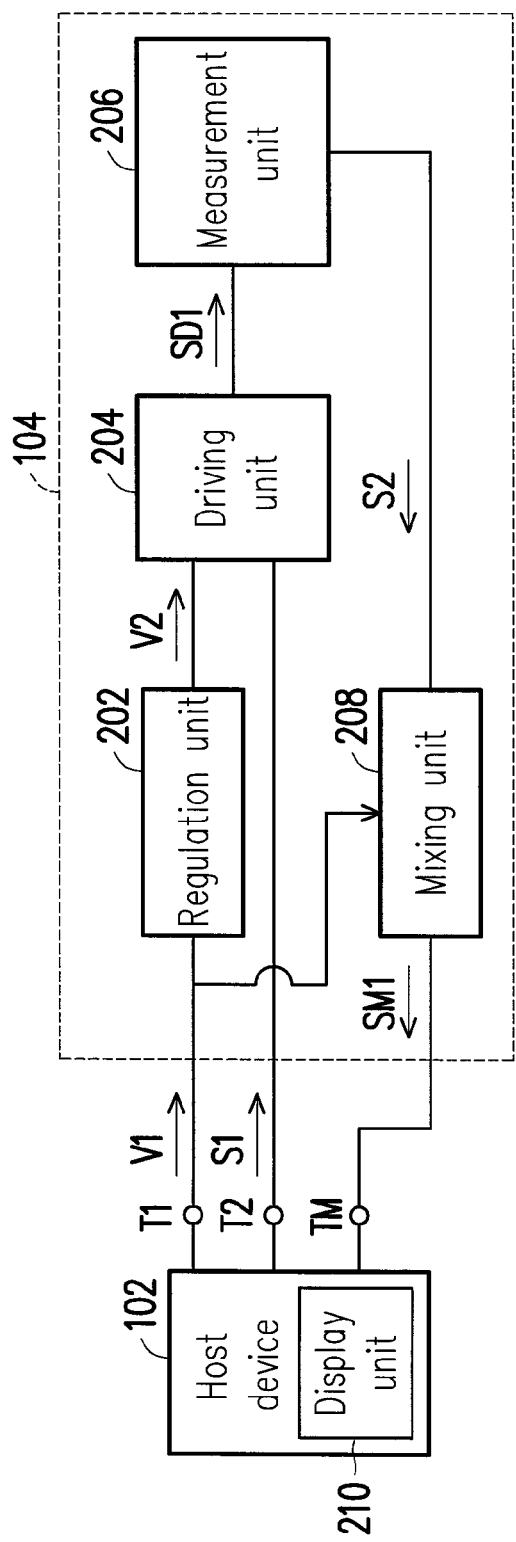
FIG. 2 is a schematic diagram of a bioelectrical impedance measurement apparatus according to another embodiment of the invention.

FIG. 2 is a schematic diagram of a bioelectrical impedance measurement apparatus according to another embodiment of the invention. Referring to FIG. 2, the measuring device 104 may include a regulation unit 202, a driving unit 204, a measurement unit 206 and a mixing unit 208. The regulation unit 202 is coupled to the sound channel output terminal T1 and the driving unit 204, the driving unit 204 is coupled to the sound channel output terminal T2 and the measurement unit 206, and the mixing unit 208 is coupled to the sound channel output terminal T1, the microphone input terminal TM and the measurement unit 206.

The regulation unit 202 receives the AC power signal V1 from the sound channel output terminal T1, and regulates the AC power signal V1 to provide a direct current (DC) power signal V2 to the driving unit 204. The driving unit 204 receives the DC power signal V2 from the regulation unit 202 and the frequency regulation signal S1 from the host device 102, and outputs a driving signal SD1 to the measurement unit 206 according to the DC power signal V2 and the frequency regulation signal S1, so as to drive the measurement unit 206 to measure the object to be tested. The measurement unit 206 outputs a measurement signal S2 obtained after measuring the object to be tested to the mixing unit 208. The mixing unit 208 mixes the received measurement signal S2 and the AC power signal V1 to convert the measurement signal S2 from a DC signal to an AC signal to produce a mixed signal SM1, and outputs the mixed signal SM1 to the microphone input terminal TM of the host device 102. The host device 102 can analyse the mixed signal SM1 to obtain the biomedical information. Moreover, the host device 102 may include a display unit 210, and the display unit 210 can display the biomedical information obtained by the host device 102 after analysing the mixed signal SM1.

Figure 3:
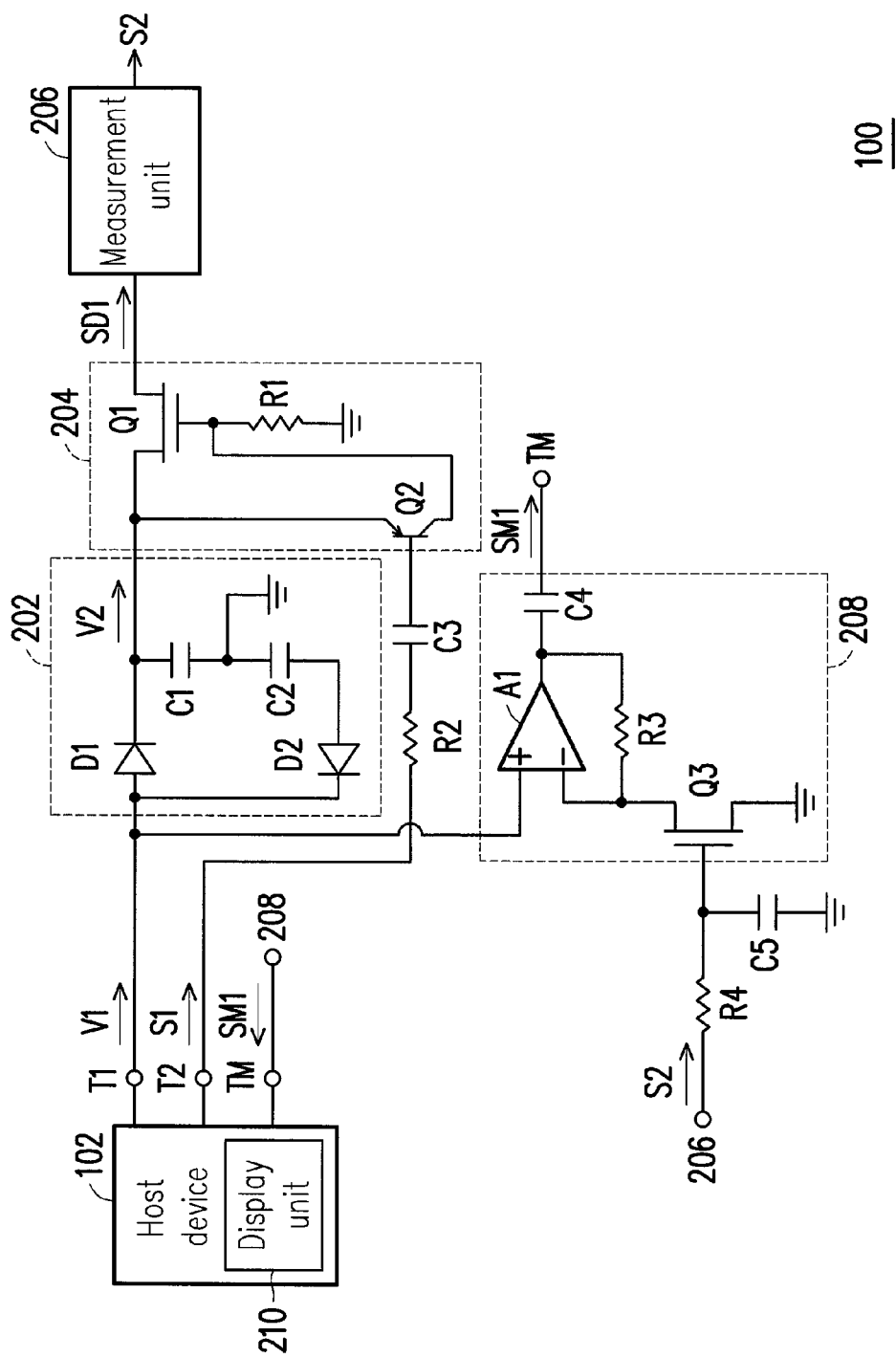
FIG. 3 is a schematic diagram of a bioelectrical impedance measurement apparatus according to another embodiment of the invention.

FIG. 3 is a schematic diagram of a bioelectrical impedance measurement apparatus according to another embodiment of the invention. Referring to FIG. 3, in detail, implementation of the bioelectrical impedance measurement apparatus 100 is as that shown in FIG. 3, though the invention is not limited thereto. In the embodiment of FIG. 3, the regulation unit 202 includes diodes D1 and D2 and capacitors C1 and C2, where an anode and a cathode of the diode D1 are respectively coupled to the sound channel output terminal T1 and the driving unit 204. The capacitor C1 is coupled between the cathode of the diode D1 and a ground. The diode D2 and the capacitor C2 are connected in series between the anode of the diode D1 and the ground. The regulation circuit formed by the diodes D1 and D2 and the capacitors C1 and C2 regulates the AC power signal V1 into the DC power signal V2, and outputs the DC power signal V2 to the driving unit 204 through the cathode of the diode D1.

Moreover, the driving unit 204 includes a transistor Q1, a bipolar transistor Q2 and a resistor R1. A drain and a source of the transistor Q1 are respectively coupled to the cathode of the diode D1 in the regulation unit 202 and the measurement unit 206. The resistor R1 is coupled between a gate of the transistor Q1 and the ground. An emitter of the bipolar transistor Q2 is coupled to the regulation unit 202, a collector thereof is coupled to the gate of the transistor Q1, and a base thereof is coupled to the sound channel output terminal T2. A frequency of turning on/off the bipolar transistor Q2 is controlled by the frequency regulation signal S1 received by the base thereof, and a turning on/off state of the bipolar transistor Q2 determines whether to output the DC power signal V2 at the drain of the transistor Q1 to the measurement unit 206 to serve the driving signal SD1. Namely, under control of the frequency regulation signal S1, the driving unit 204 can drive the measurement unit 206 through a frequency required in measurement of the measurement unit 206. In the present embodiment, the bioelectrical impedance measurement apparatus 100 further includes a resistor R2 and a capacitor C3, which are coupled in series between the sound output terminal T2 and the base of the bipolar transistor Q2, and are used to filter a DC component of the frequency regulation signal S1.

Moreover, the mixing unit 208 includes an operation amplifier A1, a resistor R3, a capacitor C4 and a transistor Q3. A positive input terminal of the operation amplifier A1 is coupled to the sound channel output terminal T1. The resistor R3 is coupled between a negative input terminal and an output terminal of the operation amplifier A1. The capacitor C4 is coupled between the output terminal of the operation amplifier A1 and the microphone input terminal TM. The transistor Q3 is coupled between the negative input terminal of the operation amplifier A1 and the ground.

A gate of the transistor Q3 receives the measurement signal S2 from the measurement unit 206. In the present embodiment, a regulation circuit formed by a resistor R4 and a capacitor C5 is further included between the measurement unit 206 and the gate of the transistor Q3, and the regulation circuit is used to regulate the measuring signal S2 to implement high-pass filtering. The resistor R4 is coupled between the measurement unit 206 and the gate of the transistor Q3, and the capacitor C5 is coupled between the gate of the transistor Q3 and the ground. After the measurement signal S2 and the AC power signal V1 are mixed by the mixing unit 208, the measurement signal S2 is changed from the DC signal into the AC signal, and the mixed signal SM1 containing the biomedical information is produced and output to the microphone input terminal TM. The host device 102 analyses the mixed signal SM1 and displays the biomedical information obtained after analysing the mixed signal SM1 through the display unit 210.

In summary, the power signal and the frequency regulation signal required for driving the measurement unit to perform measurement are provided through the sound channel output terminals of the host device, and the microphone input terminal of the host device is used to receive the measurement result, such that the host device can analyse the measurement result to obtain the biomedical information. In this way, the bioelectrical impedance measurement apparatus is adapted to a plurality of test projects of different frequencies, and can be used in collaboration with a portable electronic apparatus such as a mobile phone, a tablet PC or a notebook computer, and has characteristics of lightness, slimness, shortness and smallness and is easy to use.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A bioelectrical impedance measurement apparatus, comprising:
    a measuring device; and
    a host device, coupled to the measuring device, having a first channel output terminal, a second channel output terminal and a microphone input terminal, respectively outputting an alternating current (AC) power signal and a frequency regulation signal to the measuring device through the first channel output terminal and the second channel output terminal according to a measurement mode of the host device, so as to drive the measuring device to perform bioelectrical impedance measurement on an object to be tested, and receiving a measurement result of the object to be tested through the microphone input terminal, so as to analyse the measurement result to obtain biomedical information.

2. The bioelectrical impedance measurement apparatus as claimed in claim 1, wherein the measuring device comprises:
    a regulation unit, coupled to the first channel output terminal and the driving unit, and regulating the AC power signal to provide a direct current (DC) power signal to the driving unit;
    a driving unit, coupled to the host device, and outputting a driving signal according to the frequency regulation signal and the DC power signal;
    a measurement unit, coupled to the driving unit, driven by the driving signal to measure the object to be tested, and outputting a measurement signal; and
    a mixing unit, coupled to the microphone input terminal, the first channel output terminal and the measurement unit, and mixing the AC power signal and the measurement signal to produce a mixed signal and outputting the same to the microphone input terminal, wherein the host device analyses the mixed signal to obtain the biomedical information.

3. The bioelectrical impedance measurement apparatus as claimed in claim 2, wherein the driving unit comprises:
    a transistor, having a drain and a source respectively coupled to the regulation unit and the measurement unit;
    a resistor, coupled between a gate of the transistor and a ground; and
    a bipolar transistor, having an emitter coupled to the regulation unit, a collector coupled to the gate of the transistor, and a base coupled to the second channel output terminal.

4. The bioelectrical impedance measurement apparatus as claimed in claim 2, wherein the regulation unit comprises:
    a first diode, having an anode coupled to the first channel output terminal, a cathode coupled to the driving unit, wherein and providing the DC power signal to the drivinu unit through the cathode;
    a first capacitor, coupled between the cathode of the first diode and a ground;
    a second diode, having a cathode coupled to the anode of the first diode; and
    a second capacitor, coupled between an anode of the second diode and the ground.

5. The bioelectrical impedance measurement apparatus as claimed in claim 2, wherein the mixing unit comprises:
    an operation amplifier, having a positive input terminal coupled to the first channel output terminal;
    a capacitor, coupled between an output terminal of the operation amplifier and the microphone input terminal;
    a resistor, coupled between a negative input terminal and the output terminal of the operation amplifier; and
    a transistor, coupled between the negative input terminal of the operation amplifier and a ground, wherein a gate of the transistor is coupled to an output terminal of the measurement unit.

6. The bioelectrical impedance measurement apparatus as claimed in claim 1, wherein the host device further comprises:
    a display unit, displaying the biomedical information.

7. The bioelectrical impedance measurement apparatus as claimed in claim 1, wherein the host device comprises a mobile phone, a tablet personal computer (PC) or a notebook computer.

8. The bioelectrical impedance measurement apparatus as claimed in claim 1, wherein the measurement mode comprises an acupoint detection mode, a body fat measuring mode or a bio-detection mode.

* * * * *